US00PP22682P2

(12) United States Plant Patent
Sakazaki

(10) Patent No.: US PP22,682 P2
(45) Date of Patent: Apr. 24, 2012

(54) ***RHODANTHEMUM* PLANT NAMED 'USRHOD0701'**

(50) Latin Name: *Rhodanthemum hybrida*
Varietal Denomination: USRHOD0701

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 21 days.

(21) Appl. No.: 12/807,254

(22) Filed: Aug. 31, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — June Hwu

(74) *Attorney, Agent, or Firm* — C. A. Whealy

(57) ABSTRACT

A new and distinct cultivar of *Rhodanthemum* plant named 'USRHOD0701', characterized by its compact, upright and mounding plant habit; moderately vigorous growth habit; freely branching habit; early and freely flowering habit; no requirement for cool temperature treatment to initiate flowering; and daisy-type inflorescences with light violet-colored ray florets and brown-colored disc florets.

1 Drawing Sheet

Botanical designation: *Rhodanthemum hybrida.*
Cultivar denomination: 'USRHOD0701'.

BACKGROUND OF THE INVENTION

The present invention relates to a new and distinct cultivar of *Rhodanthemum* plant, botanically known as *Rhodanthemum hybrida* and hereinafter referred to by the name 'USRHOD0701'.

The new *Rhodanthemum* plant is a product of a planned breeding program conducted by the Inventor in Higashiomi, Shiga, Japan. The objective of the breeding program is to create new early-flowering *Rhodanthemum* plants with compact plant habit and attractive inflorescence coloration.

The new *Rhodanthemum* plant originated from a cross-pollination made by the Inventor on Feb. 10, 2005 of a proprietary selection of *Rhodanthemum hybrida* identified as code number 05RHOD05, not patented, as the female, or seed, parent with a proprietary selection of *Rhodanthemum hybrida* identified as code number 05RHOD02, not patented, as the male, or pollen, parent. The new *Rhodanthemum* plant was discovered and selected by the Inventor as a single flowering plant with the progeny of the stated cross-pollination grown in a controlled greenhouse environment in Bonsall, Calif. on Mar. 19, 2007.

Asexual reproduction of the *Rhodanthemum* plant by vegetative cuttings in Bonsall, Calif. since Mar. 26, 2007, has shown that the unique features of this new *Rhodanthemum* plant are stable and reproduced true to type in successive generations.

SUMMARY OF THE INVENTION

Plants of the new *Rhodanthemum* have not been observed under all possible environmental conditions. The phenotype may vary somewhat with variations in environment such as temperature and light intensity without, however, any variance in genotype.

The following traits have been repeatedly observed and are determined to be the unique characteristics of 'USRHOD0701'. These characteristics in combination distinguish 'USRHOD0701' as a new and distinct *Rhodanthemum* plant:

1. Compact, upright and mounding plant habit.
2. Moderately vigorous growth habit.
3. Freely branching habit.
4. Early and freely flowering habit.
5. Does not require cool temperature treatment to initiate flowering.
6. Daisy-type inflorescences with light violet-colored ray florets and brown-colored disc florets.

Plants of the new *Rhodanthemum* differ from plants of the female parent selection in the following characteristics:

1. Plants of the new *Rhodanthemum* have larger inflorescences than plants of the female parent selection.
2. Plants of the new *Rhodanthemum* and the female parent selection differ in ray floret color as plants of the female parent selection have light pink-colored ray florets.

Plants of the new *Rhodanthemum* differ from plants of the male parent selection in the following characteristics:

1. Plants of the new *Rhodanthemum* are faster growing than plants of the male parent selection.
2. Plants of the new *Rhodanthemum* flower earlier than plants of the male parent selection.
3. Plants of the new *Rhodanthemum* and the male parent selection differ in ray floret color as plants of the male parent selection have white-colored ray florets.

Plants of the new *Rhodanthemum* can be compared to plants of *Rhodanthemum* 'African Eyes', not patented. In side-by-side comparisons conducted in Bonsall, Calif., plants of the new *Rhodanthemum* differed from plants of 'African Eyes' in the following characteristics:

1. Plants of the new *Rhodanthemum* flowered earlier than plants of 'African Eyes'.
2. Plants of the new *Rhodanthemum* had larger inflorescences than plants of 'African Eyes'.

BRIEF DESCRIPTION OF THE PHOTOGRAPHS

The accompanying colored photographs illustrate the overall appearance of the new *Rhodanthemum* plant showing the colors as true as it is reasonably possible to obtain in colored reproductions of this type. Colors in the photographs may differ slightly from the color values cited in the detailed botanical description which accurately describe the actual colors of the new *Rhodanthemum* plant.

The photograph at the bottom of the sheet comprises a side perspective view of a typical flowering plant of 'USRHOD0701' grown in a container.

The photograph at the top of the sheet is a close-up view of a typical flowering plant of 'USRHOD0701'.

DETAILED BOTANICAL DESCRIPTION

Plants used for the aforementioned photographs and following description were grown under conditions which closely approximate commercial *Rhodanthemum* production conditions during the spring in 15.25-cm containers in an outdoor nursery in Bonsall, Calif. During the production of the plants, day temperatures ranged from 12° C. to 29° C., night temperatures ranged from 8° C. to 16° C. and light levels ranged from 7,000 to 10,000 foot-candles. Plants were pinched one time and were eleven weeks old when the photographs and description were taken. In the following description, color references are made to The Royal Horticultural Society Colour Chart, 2007 Edition, except where general terms of ordinary dictionary significance are used.

Botanical classification: *Rhodanthemum hybrida* 'USRHOD0701'.

Parentage:

*Female parent.*—Proprietary selection of *Rhodanthemum hybrida* identified as code number 05RHOD05, not patented.

*Male parent.*—Proprietary selection of *Rhodanthemum hybrida* identified as code number 05RHOD02, not patented.

Propagation:

*Type cutting.*—Vegetative tip cuttings.

*Time to initiate roots, summer.*—About seven days at temperatures ranging from 18° C. to 29° C.

*Time to initiate roots, winter.*—About six days at temperatures ranging from 17° C. to 21° C.

*Time to produce a rooted plant, summer.*—About 35 days at temperatures ranging from 18° C. to 29° C.

*Time to produce a rooted plant, winter.*—About 25 days at temperatures ranging from 17° C. to 21° C.

*Root description.*—Medium in thickness, fibrous; tan in color.

*Rooting habit.*—Moderately freely branching; medium in density.

Plant description:

*Form.*—Compact, upright and mounded plant habit; inverted triangle; freely branching habit with about twelve primary lateral branches each primary lateral branch with several secondary lateral branches, pinching enhances lateral branch development; moderately vigorous growth habit.

*Plant height.*—About 17 cm.

*Plant width.*—About 22 cm.

*Lateral branch description.*—Length: About 17 cm. Diameter: About 2.5 mm. Internode length: About 1 cm to 1.2 cm. Strength: Strong. Texture: Pubescent, lanulose; longitudinally ridged. Color: Close to 190A.

Foliage description:

*Arrangement.*—Alternate, simple.

*Length.*—About 3.8 cm.

*Width.*—About 1.5 cm.

*Shape.*—Roughly lanceolate, deeply dissected.

*Apex.*—Acute.

*Base.*—Attenuate, clasping.

*Margin.*—Deeply dissected with seven to nine lobes.

*Texture, upper and lower surfaces.*—Pubescent, lanulose; succulent.

*Venation pattern.*—Pinnate.

*Color.*—Developing leaves, upper and lower surfaces: Close to 189A. Fully expanded leaves, upper surface: Close to 147A; venation, close to 147A. Fully expanded leaves, lower surface: Close to N137A; venation, close to N137A.

*Petioles.*—Length: About 1 cm. Diameter: About 2 mm. Texture, upper and lower surfaces: Pubescent, lanulose. Color, upper surface: Close to 147A. Color, lower surface: Close to N137A.

Inflorescence description:

*Inflorescence arrangement, form and habit.*—Rotate daisy-type composite inflorescences; inflorescences terminal; freely flowering habit with about 26 inflorescences developing per plant; inflorescences held above the foliar plane on strong and upright peduncles; inflorescences face upright.

*Natural flowering season.*—Early flowering habit; plants do not require a cool treatment for inflorescence initiation; plants begin flowering about eleven weeks after planting; in the garden, plants flower from the spring until the autumn in Southern California.

*Inflorescence longevity on the plant.*—Inflorescences typically last about two weeks on the plant; inflorescences persistent.

*Fragrance.*—None detected.

*Inflorescence buds.*—Length: About 1.2 cm. Diameter: About 1.6 cm. Shape: Spherical. Color: Close to N87D.

*Inflorescence diameter.*—About 4.2 cm.

*Inflorescence height.*—About 1.5 cm.

*Disc diameter.*—About 1.8 cm.

*Receptacle diameter.*—About 2 cm.

*Receptacle height.*—About 9 mm.

*Receptacle color.*—Close to 191A.

*Ray florets.*—Shape: Broadly ligulate. Apex: Emarginate. Base: Attenuate. Margin: Entire. Aspect: Initially upright to nearly horizontal with development. Length: About 1.5 cm. Width: About 7 mm. Texture, upper and lower surfaces: Smooth, glabrous; longitudinally ridged. Quantity per inflorescence: About 28 arranged in 2 to 2.5 whorls. Color: When opening, upper surface: Close to 84C; towards the base, close to NN155D. When opening, lower surface: Close to 84B to 84C. Fully opened, upper surface: Close to 84B; color fading to N155C with development. Fully opened, lower surface: Close to NN155D with longitudinal streaks of close to 77C; color fading to NN155D with development.

*Disc florets.*—Shape: Tubular, narrow, fused. Apex: Acute, five-pointed. Base: Fused into a narrow tube. Margin: Entire. Length: About 7 mm. Width: About 2 mm. Texture, upper and lower surfaces: Smooth, glabrous. Quantity per inflorescence: About 360. Color, immature and mature: Apex: Close to 200B. Mid-section: Close to 195C. Base: Close to 195D.

*Involucral bracts* (*phyllaries*).—Quantity per inflorescence: About 56 arranged in about three imbricate whorls. Length: About 8 mm. Width: About 3 mm. Shape: Narrowly elliptical. Apex: Acute. Base: Truncate. Margin: Entire. Texture, upper surface: Smooth, glabrous. Texture, lower surface: Pubescent. Color, upper surface: Close to 146A; towards the margins, close to 146C. Color, lower surface: Close to 191A to 191B.

*Peduncles.*—Length: About 8.8 cm. Diameter: About 2 mm. Angle: Mostly upright to curving upwards. Strength: Strong. Texture: Pubescent. Color: Close to 191B.

*Reproductive organs.*—Androecium: (present on disc florets only). Quantity per floret: Five. Filament length: About 3.5 mm. Filament color: Close to 145D. Anther shape: Elongated oblong. Anther length: About 2 mm. Anther color: Close to 199D. Pollen amount: Scarce to moderate. Pollen color: Close to 1A. Gynoecium: (present on both ray and disc florets). Quantity per floret: One. Pistil length: About 8 mm. Stigma shape: Bi-parted. Stigma color: Close to 200B. Style length: About 3 mm. Style color: Close to 145D. Ovary color: Close to 145C.

*Seed/fruit.*—Seed and fruit production has not been observed.

Disease/pest resistance: Plants of the new *Rhodanthemum* have not been noted to be resistant to pathogens and pests common to *Rhodanthemum.*

*Garden performance.*—Plants of the new *Rhodanthemum* have been observed to have good garden performance and to tolerate temperatures from about −9° C. to about 43° C.

It is claimed:

1. A new and distinct *Rhodanthemum* plant named 'USRHOD0701' as illustrated and described.

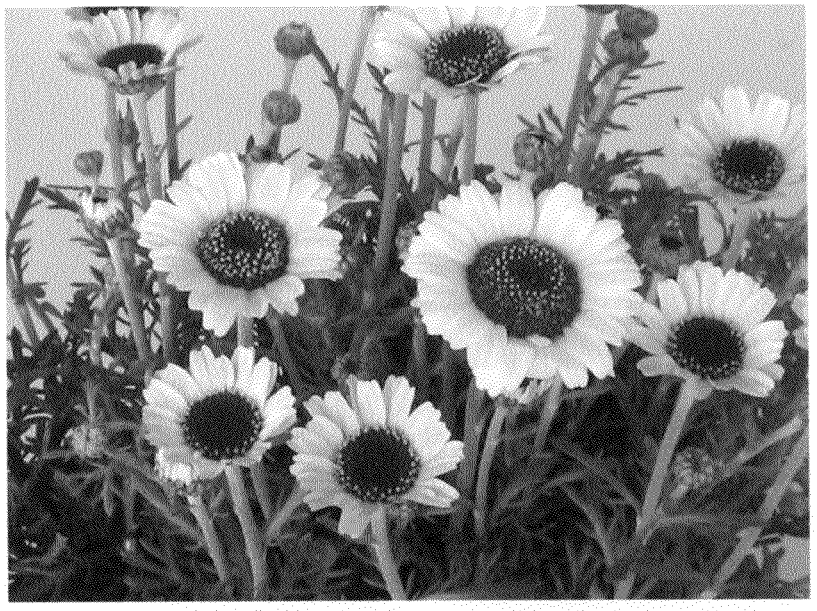
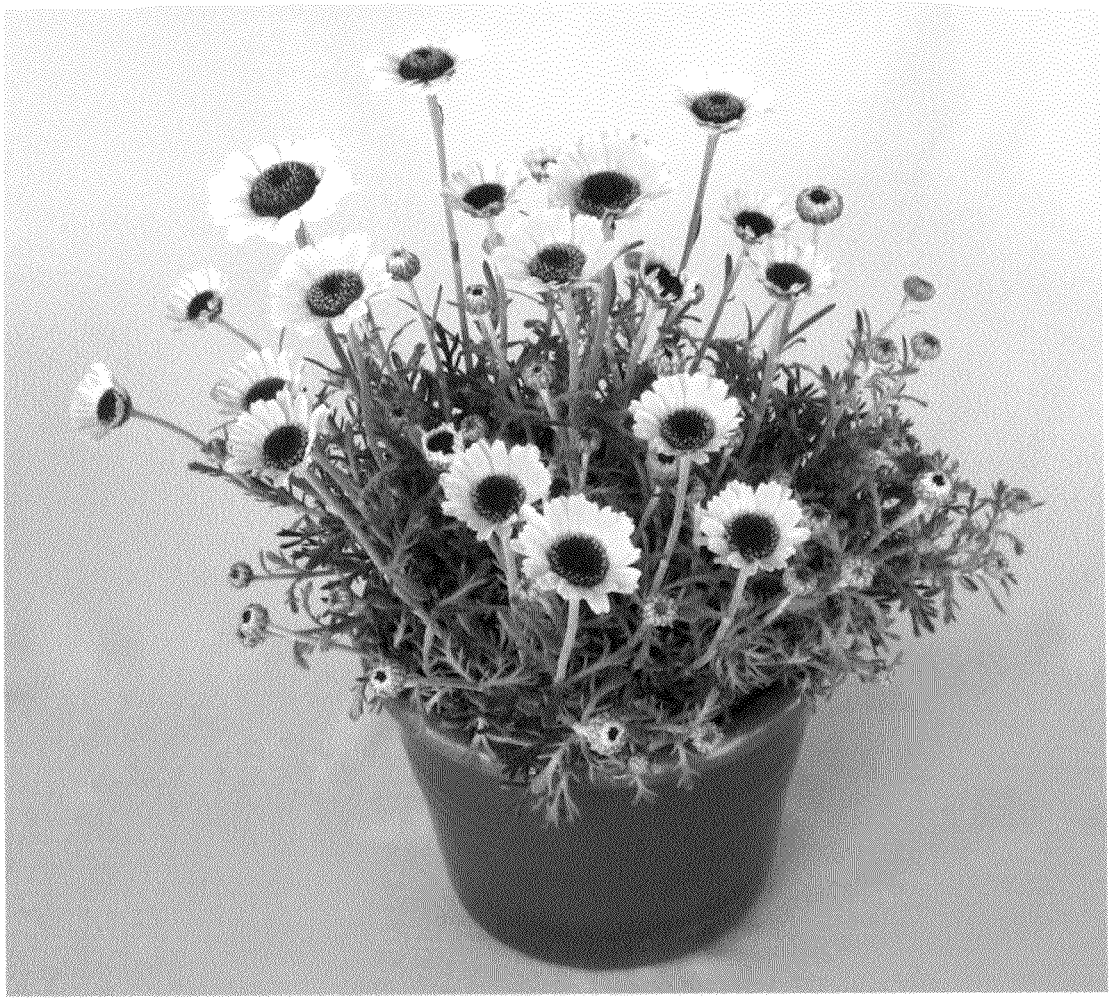

* * * * *